US00PP08683P

United States Patent [19]

Smalley et al.

[11] Patent Number: Plant 8,683

[45] Date of Patent: Apr. 12, 1994

[54] ELM TREE NAMED "CATHEDRAL"

[75] Inventors: Eugene Smalley, Cottage Grove, Wis.; Donald T. Lester, Vancouver, Canada

[73] Assignee: Wisconsin Alumni Research Foundation, Madison, Wis.

[21] Appl. No.: 857,885

[22] Filed: Mar. 26, 1992

[51] Int. Cl.[5] ..... A01H 5/00

[52] U.S. Cl. ..... Plt./53.3

[58] Field of Search ..... Plt. 53.3

[56] References Cited

PUBLICATIONS

Smalley, E. B. and D. T. Lester, "Sapporo Autumn Gold Elm," *Hortscience* vol. 8(6): 514–515 (1973).

*Primary Examiner*—James R. Feyrer
*Assistant Examiner*—Erich E. Veitenheimer
*Attorney, Agent, or Firm*—Quarles & Brady

[57] ABSTRACT

A new and distinct variety of elm tree which is characterized by its resistance to Dutch elm disease caused by *Ophiostoma ulmi* (Buisman) Nannf. Trees of this variety are also highly tolerant to Verticillium wilt disease, limited susceptibility to black leaf spot disease, and good resistance of traumatic injury from climatic elements.

4 Drawing Sheets

FIELD OF THE INVENTION

The present invention relates to a new and distinct variety of elm tree which is characterized by its resistance to Dutch elm disease caused by *Ophiostoma ulmi* (Buisman) Nannf. Trees of this variety are also highly tolerant to Verticillium wilt disease, limited susceptibility to black leaf spot disease, and good resistance of traumatic injury from climatic elements.

This new elm variety is a related sibling to variety "Sapporo Autumn Gold" which was the subject of U.S. Plant Pat. No. 3,780. Like the variety Sapporo Autumn Gold, this variety is a result of efforts to identify and propagate elm tree varieties which are aesthetically pleasing and resistant to pathogens which have seriously depleted native North American elm species, in particular the Dutch elm disease.

The "Cathedral" elm tree is a hardy new cultivar characterized by large leaves and either an up-right or spreading form, depending upon the planting distance between individuals. In dense forest plantations, the tree develops a single dominant stem, while in solitary or park plantings it develops a dense, spreading growth habit. Thus the tree has the advantage of being ideal both for forestry use as well as for horticultural, urban or street tree settings.

The accompanying FIG. 1 shows a specimen tree of the new variety planted in a park-like setting. This photograph illustrates the spreading form of the tree's habit and the general coloration and characteristics of the tree.

Origin

All ramets of the "Cathedral" elm are derived from a single disease-resistant individual grown from an open-pollinated seed which was collected from a single Siberian elm, *Ulmus pumila* L., growing in the Botanical Garden of Hokkaido University, Sapporo, Japan. The maternal parent's location in the Botanical Garden, the physical traits of the progeny, and controlled hybridization experiments (see Lester, D. T., and E. B. Smalley, Response of Backcross Hybrids and 3-species combinations of *Ulmus pumila, U. japonica*, and *U. rubra* to inoculation with Ceratocystis ulmi, Phytopathology, 62:845–848 (1973) and Lester, D. T. and E. B. Smalley, Improvement of Elms Through Interspecific Hybridization With Asian Species. IUFRO Genetics-SABRAO Joint Symposia, Tokyo, C-5(V), p. 1–10 (1972), both cited in E. B. Smalley and D. T. Lester, *HortScience*, vol. 8(6), December 1973, p. 514) indicate that the tree is an $F_1$ hybrid between *U. pumila* and *U. japonica* (Rehd.) Sarg. Thus the "Cathedral" elm is a sibling of the "Sapporo Autumn Gold" elm, but differs from "Sapporo Autumn Gold" in that it resembles its paternal parent in leaf size and general habit whereas "Sapporo Autumn Gold" more closely resembles its maternal parent.

DESCRIPTION

Figure 1:
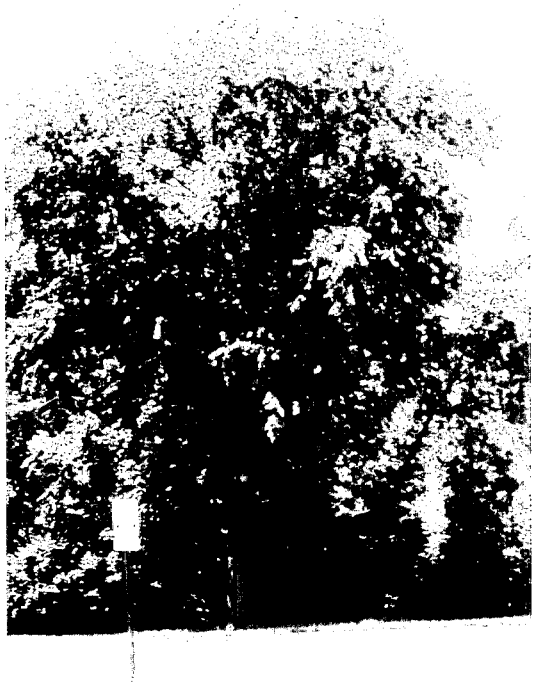
FIG. 1 shows the general habit of the claimed tree.
Figure 2:
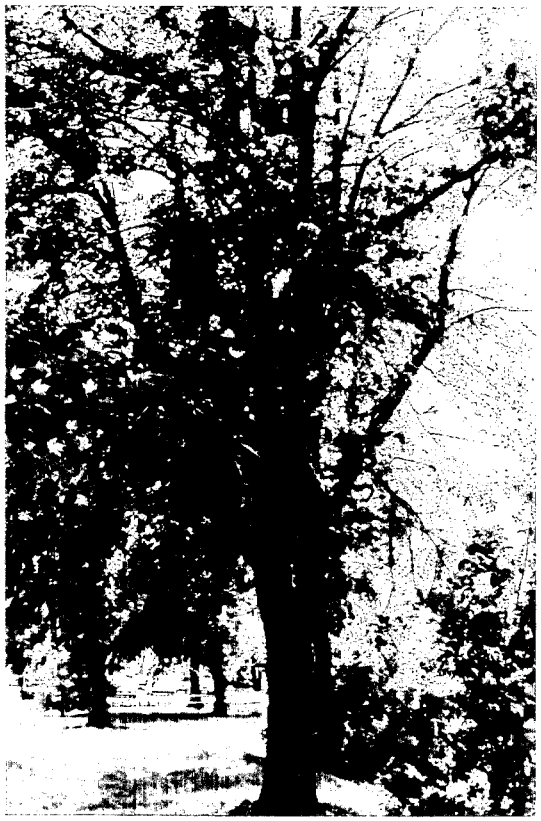
FIG. 2 shows the branching pattern of the claimed tree.

Soon after planting in a forest location, the trees of the "Cathedral" elm variety develop a strong central leader which tends to dominate and suppress extensive lateral branch development. After twenty years in replicated seasonal susceptibility field plots at a spacing of 2' by 8' in initial planting, trees of this variety and another sibling (W44-26) dominate the planting and less vigorous clones no longer are able to survive. The wood produced by trees growing under such conditions is dense, light brown in color, and resembles the wood of the European field elm (*U. carpinifolia* Gleditsch). Older trees planted at dense initial spacing may be useful at harvest as veneer logs or for high quality hardwood. The open grown trees in fertile, well drained soils exhibit a more spreading form and at maturity can become very large with a mature architecture resembling the paternal parent (*U. japonica*). FIG. 1 illustrates such an architecture. The branching pattern of Cathedral Elm is depicted in FIG. 2 which reveals approximately 30° crotch angles of the major scaffolding branches. Young trees growing at wide spacing are densely foliated. This combination of traits makes trees of this variety an excellent choice for lawn or park plantings, especially where sufficient space is available for full mature crown development. The ultimate size of Cathedral Elm is unknown however ultimate heights in excess of about 75 feet are anticipated.

Figure 3:
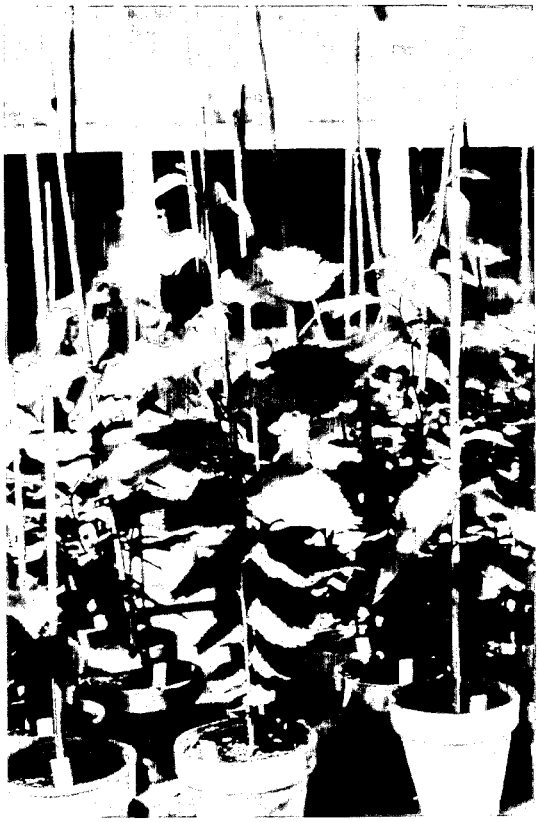
FIG. 3 shows early stage growth of the claimed tree.

New spring growth on the developing, moderately-pubescent shoots is fern green in color ($_{8}$62/1—Wilson, Horticultural Colour Chart Volume 2, British Color Council, London (1941)). FIG. 3 shows shoot growth at about one month after planting a small rooted cutting. In that one month period, the trees grew about eighteen inches. The shoots are tinged on their upper surface with brick red ($_{0}$16/3) to signal red ($_{7}$19/3). As leaves mature, they change first to a glossy parsley green ($_{0}$962) and then to a mature spinach green ($_{0}$960). The mature leaves exposed to full sun are nearly elliptical, are obtuse, and are equal at the base, acuminate at the tip, doubly serrate at the leaf margins, 12.0 to 14.0 cm long to 6.0 cm to 8.0 cm wide. Shaded leaves or leaves on a highly vigorous sprout are slightly larger. Pubescence tends to be juvenile characteristic found mainly on the more vigorous shoots, while leaves on less vigorous branches are always glabrous. All phases of pubescence can be found on a single, individual tree. Leaves become a vivid, semi-transparent, pale pea green (61/2) and then mature to a glowing yellow ocher ($_{0}$7) or cadmium orange (8/10) in the fall with this overall color holding well for many days prior to leaf drop.

Figure 4:
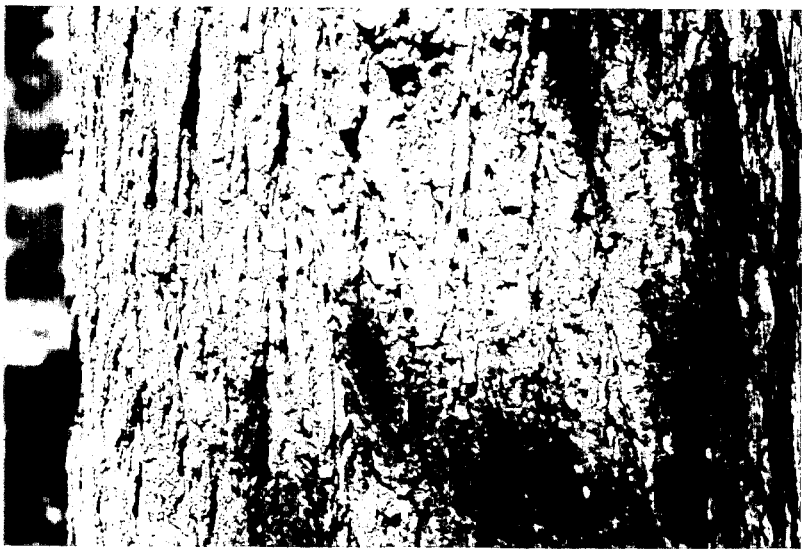
FIG. 4 shows the bark of the claimed tree.

Apical dominance is strong and results in a limited side branch development on shoots of the current season's growth. Branchlets that form the second year tend to develop dense foliage which results in a heavy leaf canopy and produces a dense shade underneath the tree. The mature bark characteristics are similar to the sibling variety "Sapporo Autumn Gold." FIG. 4 depicts the mature bark of the "Cathedral" elm.

The original tree of the line flowered first at the age of five years. Early flowering is typical of the paternal parent, and the floral and seed characteristics are not distinctive, but tend generally to resemble other varieties of the *U. japonica* species. Cathedral Elm is a very high producer of seed. The tree has been used as a male and female parent in numerous controlled crosses and is a very fertile trees, resembling its maternal parent (*U. pumila*). Early flowering refers to the tree age, rather than to the bloom date. The bloom date to Cathedral Elm, like all elms, is highly variable. Flower bud break in Madison, Wis. ranges from early to mid-April. In 1993, pollen collection was completed on April 29. Flowers would have begun to open on about April 20. In Madison, Wis., the spring temperatures largely determine the flowering date of this elm.

Disease Resistance

Trees of the elm variety "Cathedral" have exhibited superior resistance to infection by *O. ulmi*, following screening for DED resistance using the methods described in Lester, *Search* 8:39–42 (1978); and Sinclair, et al., *Plant Disease Reporter* 58:784–788 (1974). The results of a screening for resistance to Dutch elm disease of this variety and a series of elm hybrid clones is summarized in Table I. In the screening summarized in Table I, the elm clones were all derived from trees previously symptomless following one or more inoculations with *Ophiostoma ulmi*. The inoculum was a mixture of isolates of *O. ulmi* from Wisconsin, Kansas, Massachusetts, Illinois, Nebraska, Minnesota, New York, Connecticut and Maine. The trees were planted as rooted cuttings, 3 plants per clone per block, 15 clones per block, and in 40 blocks. Some clones were incompletely represented due to transplant mortality or shortage of plants and not all clones studied are listed. The clone 44-25 is the "Cathedral" elm.

TABLE I

Seasonal susceptibility of selected elm clones to Dutch elm disease
Percent crown damage at final reading (Aug 22)

| Elm species | Clone number | Dates of inoculation of three year old trees | | | | |
|---|---|---|---|---|---|---|
| | | 5/23 | 5/30 | 6/06 | 6/13 | 6/20 |
| *U. pumila* × *U. rubra* | 8-3 | 86.3 | 84.2 | 100.0 | 66.7 | 51.4 |
| *U. americana* | M-8 | 40.5 | 87.5 | 40.0 | 68.2 | 34.3 |
| *U. japonica* × *U. japonica* | 43-2 | 0.0 | 0.8 | 5.0 | 9.5 | 0.0 |
| *U. japonica* × *U. japonica* | 43-8 | 0.0 | 12.0 | 0.0 | 0.0 | 0.0 |
| *U. pumila* × *U. japonica* | 44-2 | 66.7 | 100.0 | 100.0 | 66.0 | 72.1 |
| *U. pumila* × *U. japonica* | 44-5 | 0.0 | 0.0 | 0.0 | 0.0 | 0.0 |
| *U. pumila* × *U. japonica* | 44-8 | 0.0 | 0.0 | 0.0 | 0.0 | 0.0 |
| *U. pumila* × *U. japonica* | 44-20 | 1.0 | 0.0 | 0.0 | 2.9 | 0.0 |
| *U. pumila* × *U. japonica* | 44-22 | 0.0 | 10.0 | 0.0 | 0.0 | 0.0 |
| *U. pumila* × *U. japonica* | 44-25 | 0.0 | 0.0 | 0.0 | 14.0 | 0.0 |
| *U. pumila* × *U. japonica* | 44-26 | 7.1 | 0.0 | 0.0 | 4.2 | 0.0 |
| *U. pumila* × *U. pumila* | 337-9 | 0.0 | 0.0 | 0.0 | 0.0 | 0.0 |

| Elm species | Clone number | Dates of inoculation of three year old trees | | | | |
|---|---|---|---|---|---|---|
| | | 6/26 | 7/03 | 7/18 | 8/02 | 8/16 |
| *U. pumila* × *U. rubra* | 8-3 | 0.0 | 24.6 | 24.6 | 24.0 | 2.8 |
| *U. americana* | M-8 | 6.3 | 0.0 | 12.5 | 0.0 | 0.3 |
| *U. japonica* × *U. japonica* | 43-2 | 0.0 | 0.0 | 3.3 | 1.0 | 0.0 |
| *U. japonica* × *U. japonica* | 43-8 | 0.0 | nd | 0.0 | nd | nd |
| *U. pumila* × *U. japonica* | 44-2 | 20.2 | 12.5 | 63.3 | 20.0 | 37.5 |
| *U. pumila* × *U. japonica* | 44-5 | 0.0 | 0.0 | 0.0 | 0.0 | 0.0 |
| *U. pumila* × *U. japonica* | 44-8 | 0.0 | 0.0 | 0.0 | 0.0 | 0.0 |
| *U. pumila* × *U. japonica* | 44-20 | 0.0 | 0.0 | 0.0 | 0.0 | 0.0 |
| *U. pumila* × *U. japonica* | 44-22 | 0.0 | 0.0 | 0.0 | 0.0 | 0.0 |
| *U. pumila* × *U. japonica* | 44-25 | 8.0 | 0.0 | 3.0 | 0.1 | 3.3 |
| *U. pumila* × *U. japonica* | 44-26 | 0.0 | 0.0 | 0.0 | 0.0 | 0.0 |
| *U. pumila* × *U. pumila* | 337-9 | 0.0 | 0.0 | 0.0 | 0.0 | 0.0 |

In general, seedlings are grown for one year in indoor seed beds or in roottrainers (Le Maire Industries) in the greenhouse, then transplanted into field locations in a second or third season. The trees are maintained under clean cultivation and are artificially inoculated with *O. ulmi* in the third or fourth year. Trees are inoculated in the one year old wood in the tree's upper crown with inoculum containing approximately $10^6$ spores per ml. Survivors of this procedure are re-inoculated in subsequent years. As a final test (called the "seasonal susceptibility trial"), selected resistant individuals are clonally propagated and grown in replicated field plantings for two or more years before inoculation. Different individuals of each clone are then inoculated periodically during the growing season to define a seasonal pattern of susceptibility. In this testing protocol, the inoculum consisted of a mixed conidial suspension from ten different isolates of the fungus from different North American locations. Observations on disease development are then recorded periodically throughout the year following inoculation. Trees of the elm variety "Cathedral" possess high resistant to *O. ulmi* although it is slightly less resistant than "Sapporo Autumn Gold."

Asexual Reproduction

Trees of the "Cathedral" elm cultivar can, and have, been propagated from root cuttings allowed to sprout in the greenhouse in moist sphagnum peat and sand. Greenhouse cuttings can be taken from the sprouts and dipped in commercial rooting hormone. Greenwood cuttings taken from the sprouts and dipped in rooting hormone can be transplanted as rooted cuttings after approximately twenty days in a perlite-peat rooting medium under fine intermittent mist. Propagation by grafting or budding is also possible, but the suitability of root stocks such as *U. pumila* seedlings, should be tested prior to large scale propagation to avoid possible long-term incompatibilities.

Other Characteristics

Trees of the elm variety "Cathedral" are apparently highly tolerant to *Verticillium dahliae* Kleb., the causal agent of Verticillium wilt disease. Plantings in soils known to be heavily infested have remained symptomless even when close by trees have susceptible species such as *U. laciniata* developed severe Verticillium wilt symptoms. The variety also appears to have limited susceptibility to black leaf spot disease, caused by *Stegophora ulmea*. Ice storms or severe winds have not produced injury on the parent tree or in any of the secondary plantings even when adjacent *U. pumila* trees sustain serious large branch damage. As its parental heritage might indicate, trees of the variety "Cathedral" show only limited resistance to the elm leaf beetle, and regular control measures may need to be considered in locations with severe or endemic elm leaf beetle infestations. The variety does appear, however, to be resistant to attack by the elm leaf miner *Fenusa ulmi*, an insect which over the past ten years has become a major pest on naturalized *U. pumila* and its hybrids with *U. rubra* or *U. globra*.

What is claimed is:

1. A new and distinct variety of elm tree named "Cathedral" substantially as described and illustrated herein.

* * * * *